United States Patent [19]

Gaudilliere et al.

[11] Patent Number: 4,711,899
[45] Date of Patent: Dec. 8, 1987

[54] 2-(4-BENZOYL-1-PIPERIDYL)-1-PHENYLALKANOL DERIVATIVES

[75] Inventors: Bernard Gaudilliere, Nanterre; Jean Rousseau, Bourg La Reine, both of France

[73] Assignee: Synthelabo, Paris, France

[21] Appl. No.: 862,715

[22] Filed: May 13, 1986

[30] Foreign Application Priority Data

May 14, 1985 [FR] France ............... 85 07270

[51] Int. Cl.$^4$ ............... A61K 31/445; C07D 211/32
[52] U.S. Cl. ............... 514/330; 546/225
[58] Field of Search ............... 546/225; 514/330

[56] References Cited

U.S. PATENT DOCUMENTS

| 3,576,810 | 4/1971 | Duncan, Jr. et al. | 546/225 |
| 3,579,512 | 5/1971 | Kuhnis et al | 546/225 |
| 3,632,767 | 1/1972 | Gray et al. | 546/225 X |
| 3,795,677 | 3/1974 | Carr et al. | 546/225 X |
| 4,021,564 | 5/1977 | Hernestam et al. | 546/225 X |
| 4,035,369 | 7/1977 | Vandenberk et al. | 546/198 X |
| 4,198,419 | 4/1980 | Ong et al. | 546/225 X |
| 4,335,127 | 6/1982 | Vandenberk et al. | 546/207 X |
| 4,458,076 | 7/1984 | Strupczewski | 546/225 X |
| 4,559,349 | 12/1985 | Storni | 546/225 X |

FOREIGN PATENT DOCUMENTS

| 0013612 | 7/1980 | European Pat. Off. |
| 0070053 | 1/1983 | European Pat. Off. |
| 0109317 | 5/1984 | Euorpean Pat. Off. |
| 2651554 | 5/1977 | Fed. Rep. of Germany ...... 546/225 |
| 2408602 | 11/1977 | France . |

OTHER PUBLICATIONS

Duncan, Jr., et al.; Journal of Med. Chem. 13, Jan. 1970; pp. 1–6.
Weygand/Hilgetag; "Preparative Organic Chemistry", (1972) p. 535; John Wiley & Sons, N.Y. & London.
Noller, "Chemistry of Organic Compounds, (1965), 3rd ed., pp. 257–258, 813–814; W. B. Saunders Co., Phila. & London.

Primary Examiner—Joseph Paul Brust
Attorney, Agent, or Firm—Wegner & Bretschneider

[57] ABSTRACT

Compound of general formula I

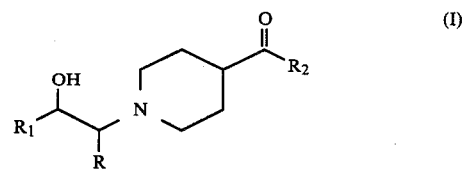

in which R is hydrogen, $R_1$ is unsubstituted phenyl, 4-methoxy - 3,5-dimethylphenyl or phenyl substituted at one of the 2-, 3- or 4- positions by halogen, $C_{1-4}$ alkyl, $C_{1-4}$ alkoxy, hydroxy, benzyloxy, trifluoromethyl, cyano, nitro, amino, acetylamino, methylthio, methylsulphonyl or aminosulphonyl and $R_2$ is unsubstituted phenyl, 2,4,6-trimethoxyphenyl or phenyl substituted at either the 3- or the 4- positions by fluorine, chlorine, methyl or methoxy, or an acid addition salt thereof.

9 Claims, No Drawings

2-(4-BENZOYL-1-PIPERIDYL)-1-PHENYLALK-ANOL DERIVATIVES

The subject of the present invention is 2-(4-benzoyl-1-piperidyl)-1-phenylalkanol derivatives, the preparation thereof and their application in therapy.

The present invention provides the compounds of formula I

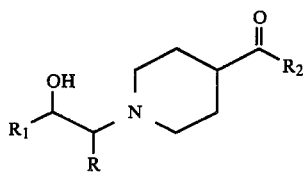

wherein
R is hydrogen or methyl,
$R_1$ is unsubstituted phenyl, 4-methoxy-3,5-dimethyl phenyl or phenyl substituted at one of the 2-, 3- or 4-positions by halogen, $C_{1-4}$alkyl, $C_{1-4}$alkoxy, hydroxy, benzyloxy, trifluoromethyl, cyano, nitro, amino, acetylamino, methylthio, methylsulphonyl or aminosulphonyl and $R_2$ is unsubstituted phenyl, 2,4,6-trimethoxyphenyl or phenyl substituted at either the 3- or the 4- position by fluorine, chlorine, methyl or methoxy, or an acid addition salt thereof.

When R denotes hydrogen, the molecules of formula I contain a single asymmetric carbon atom. They can consequently take the form of pure optical isomers or mixtures thereof.

When R denotes a methyl group, the molecules of formula I contain two vicinal asymmetric carbon atoms. There are consequently two diastereoisomeric forms, erythro and threo, each of which comprises two optical isomers.

The invention comprises each of these pure forms, and also the mixtures thereof.

Compounds of structures similar to that of the compounds of the invention are already known, by virtue of European Patent Application No. 0 109 317.

The invention also provides a process for producing compounds of formula (I) which process comprises (a) treating a compound of formula (V)

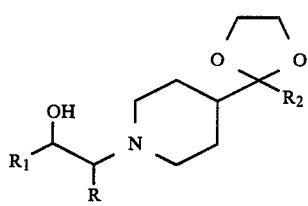

wherein R, $R_1$ and $R_2$ are as defined in relation to compounds of formula (I) with acid, preferably hydrochloric acid or formic acid, or (b) reacting a compound of formula (VI)

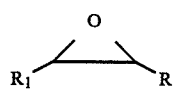

wherein R and $R_1$ are as defined in relation to compounds of formula (I) with a compound of formula (VII)

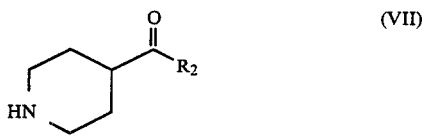

at elevated temperature and in the presence of a suitable solvent such as ethanol, preferably at the reflux temperature of the reaction mixture and optionally thereafter converting one compound of formula (I) into another compound of formula (I), converting a base of formula (I) into the corresponding salt or converting a salt into the corresponding base of formula (I).

The compound of formula (V) is preferably produced as follows:

A halogenated ketone of formula (II),

in which R and $R_1$ are as defined above and X denotes a chlorine or bromine atom, is first reacted with a dioxolanylpiperidine of formula (III),

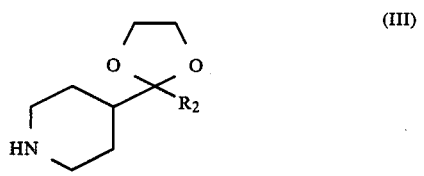

in which $R_2$ is as defined above. The reaction is preferably performed in a solvent, and in the presence of a base. The amino ketone of formula (IV)

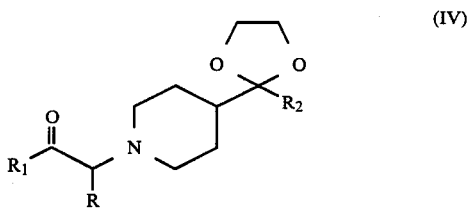

thereby obtained is then subjected to reduction, for example with an alkali metal borohydride, to give an alcohol of formula (V). When R denotes a methyl group, and depending on the conditions of the reaction, it is possible to prepare selectively the erythro or threo isomers. Thus, in the presence of an acid, especially acetic acid, a mixture rich in the erythro isomer is obtained, while in the absence of acid a mixture rich in the threo isomer is obtained. These mixtures can then be purified, for example by chromatography.

The starting halogenated ketone (II) can be obtained by known processes, as described, for example, in European Patent Application No. 0 109 317.

The dioxolanylpiperidine of formula (III) can be obtained by acetalization of the corresponding 4-benzoyl-piperidine, by methods similar to those described, for example, in European Patent Applications Nos. 0 013 612 and 0 070 053, or in U.S. Pat. No. 4,335,127 or in German Patent Application No. 2 645 125.

The epoxide (VI) can be obtained in various ways, either, when R=H, from the corresponding benzaldehyde, for example by the action of trimethylsulphonium iodide and potassium hydroxide, or from the corresponding α-bromo-acetophenone, by the action of an alkali metal borohydride followed by potassium hydroxide or, when R=H or $CH_3$, from the corresponding styrene, by oxidation with meta-chloro-perbenzoic acid.

When the epoxide (VI) is in the form of a single optical isomer, the synthesis of an optically active final compound (I) can be accomplished.

The 4-benzoylpiperidines of formula (VII) can be prepared, for example, by methods such as those described by R. L. Duncan et al. in J. Med. Chem. 1970, 13, 1–6, or by P. Manoury in the application for a French Certificate of Addition No. 2 408 602.

Finally, interconversion of the compounds in the formula (I) may involve, for instance, debenzylation of a compound of formula (I) in which $R_1$ denotes a benzyloxy-phenyl group, to produce the corresponding hydroxyphenyl compound of formula (I) or reduction of a compound of formula (I), wherein $R_1$ is nitrophenyl to produce a compound of formula (I) in which $R_1$ is aminophenyl. Similar conversions may be effected in the precursor compounds.

The compounds of the invention show anti-anoxic activity, and can be used in therapy for the treatment of disorders of alertness, especially for combating behavioral disorders attributable to cerebral vascular damage and to cerebral sclerosis in geriatrics, as well as for the treatment of metabolic encephalopathies and migraine and the treatment of cardiac and peripheral vascular disorders, and for the treatment of depressive states.

The invention consequently comprises all pharmaceutical compositions which contain the compounds and/or the salts thereof as active principles, in combination with all excipients suitable for administering them, especially orally or parenterally.

The administration routes can be the oral and parenteral routes.

The daily dosage, for instance for an adult human, can range from 1 to 100 mg parenterally and from 5 to 500 mg orally.

The following non-limiting Examples illustrate in a detailed manner the preparation of a few compounds according to the invention. The microanalyses and IR and NMR spectra of these compounds confirm their chemical structure.

EXAMPLE 1

2-[4-(4-Fluorobenzoyl)-1-piperidyl]-1-phenylethanol 2.4 g (0.02 mole) of styrene oxide, 4.9 g (0.02 mole) of 4-(4-fluorobenzoyl)piperidine hydrochloride, 2.8 g of potassium carbonate and 50 ml of ethanol are introduced in a 250-ml Erlenmeyer, and the mixture is heated under reflux for 3 h.

The solvent is driven off, and the residue is taken up with water and extracted with ether.

The organic phases are combined, washed, dried and evaporated, and this yields a crystallized product which is chromatographed on a silica column, eluting with a 96:4 chloroform/methanol mixture.

The base thus purified is taken up with 92 ml of a 0.1 N solution of hydrochloric acid in isopropyl alcohol, the alcohol is evaporated off and the residue recrystallized in isopropyl alcohol.

Melting point of the hydrochloride: 218° C.

EXAMPLE 2

2-[4-(4-Fluorobenzoyl)-1-piperidyl]-1-(4-chlorophenyl)ethanol 5.85 g (0.025 mole) of 4-chlorostyrene oxide and 5.4 g (0.026 mole) of 4-(4-fluorobenzoyl)piperidine are dissolved in 100 ml of anhydrous ethanol, and the mixture is heated under reflux for 4 h.

The alcohol is driven off under vacuum and an oily residue is obtained which crystallizes when ground in ether. The crystals are drained and the ether is evaporated off under vacuum, and a second crop of the product is obtained by grinding the solid residue in methanol.

The hydrochloride of the product is prepared and recrystallised as described in Example 1.

Melting point of the hydrochloride: 221°–223° C.

EXAMPLE 3

2-[4-(4-Fluorobenzoyl)-1-piperidyl]-1-(3-methylphenyl)ethanol 1.34 g (0.01 mole) of 3-methylstyrene oxide, 2.43 g (0.01 mole) of 4-(4-fluorobenzoyl)piperidine hydrochloride, 1.40 g of potassium carbonate and 50 ml of ethanol are introduced in a 250-ml round-bottomed flask.

The mixture is heated under reflux for 3 h, the alcohol evaporated off, and the residue taken up with water and extracted with ethyl acetate. The organic phases are combined, washed and dried, and the solvent is driven off. The residual oil crystallizes.

It is purified by chromatography and its hydrochloride is prepared as described in Example 1, the final recrystallization, however, being performed in a 2-propanol/ethanol mixture.

Melting point of the hydrochloride: 226° C.

EXAMPLE 4

2-[4-(4-Fluorobenzoyl)-1-piperidyl]-1-(4-methoxyphenyl)ethanol (a)

2-{4-[2-(4-Fluorophenyl)-1,3-dioxolan-2-yl]-1-piperidyl}-1-(4-methoxyphenyl)ethanone A mixture of 4.4 g (0.02 mole) of 2-bromo-1-(4-methoxyphenyl)ethanone, 5.75 g (0.02 mole) of 2-(4-fluorophenyl)-2-(4-piperidyl)-1,3-dioxolane hydrochloride, 2.76 g of potassium carbonate and 100 ml of acetonitrile is heated under reflux for 4 h.

The solvent is driven off, and the residue is taken up with water and dilute ammonia solution and extracted with ethyl acetate.

The organic phases are combined, washed and dried over sodium sulphate, and the solvent is evaporated off. The residue is purified by chromatography, eluting with a 99:1 chloroform/methanol mixture.

(b)

2-{4-[2-(4-Fluorophenyl)-1,3-dioxolan-2-yl]-1-piperidyl}-1-(4-methoxyphenyl)ethanol A mixture of 3 g (0.0075 mole) of the compound obtained above, 1.21 g (0.0225 mole) of potassium borohydride and 100 ml of methanol is stirred for 2 h at room temperature.

The solvent is evaporated off, the residue is taken up with a mixture of water and ethyl acetate, and the organic phase is separated, washed, dried and evaporated. The residue is recrystallized in ethanol.

Melting point: 120° C.

(c)

2-[4-(4-Fluorobenzoyl)-1-piperidyl]-1-(4-methoxyphenyl)ethanol

A mixture of 1.5 g (0.0037 mole) of the above compound and 50 ml of 2 N hydrochloric acid is heated to 100° C. for 30 minutes on an oil bath.

The mixture is allowed to cool and alkalinized with dilute ammonia solution, and the base is extracted with ethyl acetate.

The extract is washed and dried and the solvent evaporated off, and the residue is purified by chromatography, eluting with a 99:1 chloroform/methanol mixture.

To prepare the hydrochloride, a stoichiometric amount of a 0.1 N solution of hydrochloric acid in isopropyl alcohol is added to the base, equivalent to 36.3 ml for 1.3 g of base. The salt crystallizes on grinding. After evaporation of the alcohol, the product is recrystallized in a 2-propanol/ethanol mixture.

Melting point of the hydrochloride: 218° C.

EXAMPLE 5

2-[4-(4-Fluorobenzoyl)-1-piperidyl]-1-(4-fluorophenyl)-1-propanol, erythro form (a)

2-{4-[2-(4-Fluorophenyl)-1,3-dioxolan-2-yl]-1-piperidyl}-1-(4-fluorophenyl)-1-propanone.

The reaction is performed under the conditions of Example 4a, starting with 9.24 g (0.04 mole) of 2-bromo-1-(4-fluorophenyl)-1-propanone, 10.05 g (0.04 mole) of 2-(4-fluorophenyl)-2-(4-piperidyl)1,3-dioxolane and 5.56 g of potassium carbonate in 150 ml of acetonitrile.

(b)

2-{4-[2-(4-Fluorophenyl)-1,3-dioxolan-2-yl]-1-piperidyl}-1-(4-fluorophenyl)-1-propanol 10 g of the above compound are dissolved in a mixture of 150 ml of methanol and 75 ml of acetic acid, and 6.7 g of potassium borohydride are added in small portions. The mixture is stirred for 2 h, and left standing overnight.

The solvent is evaporated off, and the residual oil is taken up with ice and dilute ammonia solution and extracted with methylene chloride. After the organic phase has been washed, dried and evaporated, a crystalline product remains.

(c)

2-[4-(4-Fluorobenzoyl)-1-piperidyl]-1-(4-fluorophenyl)-1-propanol, erythro form.

A suspension of 9 g of the above compound in 300 ml of normal hydrochloric acid is heated to 100° C. for 4 h on an oil bath. The hydrochloride precipitates. It is drained, rinsed with water and then ether, dried and recrystallized in ethanol.

Melting point of the hydrochloride: 250°–252° C.

EXAMPLE 6

2-[4-(4-Fluorobenzoyl)-1-piperidyl]-1-(4-fluorophenyl)-1-propanol, threo form (a)

2-{4-[2-(4-Fluorophenyl)-1,3-dioxolan-2-yl]-1-piperidyl}-1-(4-fluorophenyl)-1-propanol 10 g of the ketone obtained according to Example 5a are dissolved in 200 ml of methanol, 6.72 of potassium borohydride are added and the mixture is stirred for 3 h at room temperature. It is left to stand overnight, the solvent is evaporated off, and the residue is alkalinized and extracted with ethyl acetate. After the organic phase has been washed, dried and evaporated, a mixture is collected in which the threo form predominates. The pure threo form is obtained by chromatography on silica, eluting with a 98:2 methylene chloride/methanol mixture.

(b)

2-[4-(4-Fluorobenzoyl)-1-piperidyl]-1-(2-fluorophenyl)-1-prapanol, threo form

The procedure is as in Example 5c.

Melting point of the hydrochloride: 245°–247° C.

EXAMPLE 7

2-[4-(4-Fluorobenzoyl)-1-piperidyl]-1-(4-hydroxyphenyl)-1-propanol, erythro form (a)

1-(4-benzoyloxyphenyl)-2-(4-[2-(4-fluorophenyl)-1,3-dioxolan-2-yl]-1-piperidyl)-1-propanone A mixture of 10.99 g (0.04 mole) of 2-chloro-1-(4-benzyloxyphenyl)-1-propanone, 10.05 g (0.04 mole) of 2-(4-fluorophenyl)-2-(4-piperidyl)-1,3-dioxolane, 5.52 g of potassium carbonate and 150 ml of acetonitrile is heated under reflux for 4 h. Working as described in Example 4a, an oil is isolated which is used as it is in the following stage.

(b)

1-(4-benzoyloxyphenyl)-2-(4-[2-(4-fluorophenyl)-1,3-dioxolan-2-yl]-1-piperidyl)-1-propanol 16 g of the oil obtained above are dissolved in a mixture of 150 ml of methanol and 50 ml of acetic acid. The solution is cooled in an ice bath and 16 g of potassium borohydride are added in small portions.

The mixture is stirred for 2 h, the solvent is evaporated off, the crystallized residue is taken up with ice-cold water and 3 N ammonia solution is added until the pH is 8, followed by 250 ml of ethyl acetate.

The mixture is stirred for 30 minutes, and the precipitate formed is drained, washed with pentane and dried.

Melting point: 144°–146° C.

(c)

1-(4-benzoyloxyphenyl)-2-[4-(4-fluorobenzoyl)-1-piperidyl]-1-(4-benzyloxy-phenyl)-1-propanol, erythro form 2.5 g of the above compound are suspended in 100 ml of 1 N hydrochloric acid, and the mixture is heated at 100° C. for 6 h. The hydrochloride which has precipitated is filtered off, rinsed with water and recrystallized in an ethanol/methanol mixture. Melting point: 242°–244° C.

(d)

2-[4-(4-Fluorobenzoyl)-1-piperidyl]-1-(4-hydroxyphenyl)-1-propanol erythro form

A mixture of 5 g of the above compound, 1 g of palladinized charcoal, 10 ml of formic acid and 200 ml of isopropyl alcohol is heated under reflux for 8 h.

The catalyst is separated by filtration and rinsed with methanol, and the filtrate is evaporated.

The dry residue is taken up with ice-cold water, 3 N ammonia solution is added until the pH is 8 and the mixture is extracted with chloroform.

After decantation, washing and drying, the organic phase is evaporated to give a crystallized white residue. 105 ml of a 0.1 N solution of hydrochloric acid in 2-propanol are added to 4 g of the base thereby obtained, the mixture is stirred, the alcohol is evaporated off and the hydrochloride is recrystallized in ethanol.

Melting point: 212°-214° C.

EXAMPLE 8

(R)-(−)-2-[4-(4-Fluorobenzoyl)-1-piperidyl]-1-phenylethanol.

A mixture of 3.6 g (0.03 mole) of (R)-(−)-phenyloxirane, 7.3 g (0.03 mole) of 4-(4-fluorobenzoyl) piperidine hydrochloride, 8.3 g (0.06 mole) of potassium carbonate and 200 ml of ethanol is heated under reflux for 2 h in a 500-ml round-bottomed flask.

The solvent is then evaporated off, the residue is taken up with water and the organic base is extracted with dichloromethane. The organic phase is washed with water, dried over sodium sulphate and evaporated. The residue is purified by chromatography on silica, eluting with a 99.5:0.5 chloroform/methanol mixture, and the hydrochloride of the purified solid is prepared by adding a 0.1 N solution of hydrochloric acid in isopropyl alcohol, and recrystallized in isopropyl alcohol.

Melting point of the hydrochloride: 205° C.

$[\alpha]_D^{20} = 34.15°$ (C=0.5%, CH$_3$OH).

EXAMPLE 9

(S)-(+)-2-[4-(4-Fluorobenzoyl)-1-piperidyl]-1-phenylethanol

A mixture of 3.24 g (0.027 mole) of (S)-(+)-phenyloxirane, 6.62 g (0.027 mole) of 4-(4-fluorobenzoyl)piperidine hydrochloride, 7.5 g (0.055 mole) of potassium carbonate and 250 ml of ethanol is heated under reflux for 3 h in a 500-ml round-bottomed flask.

The solvent is then evaporated off, the residue is taken up with a mixture of water and dichloromethane, the organic solution is separated, washed with water and dried over sodium sulphate and the solvent is driven off. The residue is purified by chromatography, eluting with a 99:1 dichloromethane/methanol mixture, and the hydrochloride of the purified solid is prepared by adding a 0.1 N solution of hydrochloric acid in isopropyl alcohol, and recrystallized in isopropyl alcohol.

Melting point of the hydrochloride: 196°-198° C.

$[\alpha]_D^{20} = +32.90°$ (C=0.5%, CH$_3$OH)

EXAMPLE 10

1-(3-Acetylaminophenyl)-2-[4-(4-fluorobenzoyl)1-piperidyl]ethanol (a)

1-(3-Acetylaminophenyl)ethanone 50 ml of acetic anhydride are added in the cold to a suspension of 30 g (0.22 mole) of 1-(3-aminophenyl)ethanone in 200 ml of toluene, and the mixture is stirred for 1 h at room temperature, then heated for 1 h to 60° C. and left to stand overnight. The precipitate obtained is drained, ground in ether and dried.

(b)

1-(3-Acetylaminophenyl)-2-bromoethanone

A mixture of 17.7 g (0.1 mole) of the above ketone, 54.56 g (0.11 mole) of pyrrolidone hydrotribromide, 9.36 g (0.11 mole) of pyrrolidone and 500 ml of tetrahydrofuran is heated under reflux.

An insoluble product is separated by filtration, rinsing it with tetrahydrofuran, the filtrate is evaporated and the residual oil taken up with dichloromethane, and the solution is washed with water, dried and evaporated. The residual oil is ground in ether. A crystallized product is obtained which is dried at room temperature under vacuum.

Melting point: 98° C.

(c)

1-(5-Acetylaminophenyl)-2-{4-[2-(4-fluorophenyl)-1,3-dioxolan-2-yl]-1-piperidyl}ethanol A mixture of 8.9 g (0.035 mole) of the above brominated ketone, 8.7 g (0.035 mole) of 4-[2-(4-fluorophenyl)-1,3-dioxolan-2-yl]piperidine and 7 g (0.08 mole) of potassium carbonate in 200 ml of ethanol is left to react for 2 h at room temperature. 12 g of potassium borohydride are then added, followed by 20 ml of acetic acid to favour the reaction kinetics, and stirring is maintained for 5 h.

The mixture is evaporated and the residue is taken up with water and dilute ammonia solution, and the base is extracted with ethyl acetate. The organic solution is washed with water, dried over sodium sulphate and evaporated, and the residue is purified by chromatography, eluting with a 98:2 dichloromethane/methanol mixture.

(d)

1-(3-Acetylaminophenyl)-2-[4-(4-fluorobenzoyl)-1-piperidyl]ethanol 2.4 g (0.0056 mole) of the above product are dissolved in 50 ml of formic acid and the solution is heated to 100° C. for 3 h. The mixture is then cast into ice-cold water, ammonia solution is added until the pH is above 8, and the organic base is extracted with ethyl acetate. The organice phase is washed with water and dried over magnesium sulphate, the solvent is driven off and the product is purified with a 98:2 dichloromethane/methanol mixture. The purified product cyrstallizes in pentane.

Melting point of the free base: 158° C.

EXAMPLE 11

1-(3-Aminophenyl)-2-[4-(4-fluorobenzoyl)-1-piperidyl]ethanol (a)

2-Bromo-1-(3-nitrophenyl)ethanone

Bromination of 1-(3-nitrophenyl)ethanol is performed under conditions similar to those described in Example 10b.

(b)

2-{4-[2-(4-Fluorophenyl)-1,3-dioxolan-2-yl]-1-piperidyl}-1-(3-nitrophenyl)ethanol The brominated ketone is reacted with 4-[2-(4-fluorophenyl)-1,3-dioxolan-2-yl]piperidine under conditions similar to those described in Example 10c.

(c)

2-{4-[2-(4-Fluorophenyl)-1,3-dioxolan-1-yl]-1-piperidyl}-1-(3-aminophenyl)ethanol Reduction of 6 g (0.0144 mole) of the above compound in 200 ml of methanol is performed under a hydrogen pressure of 0.35 MPa in the presence of 1 g of Raney nickel. After separation of the catalyst by filtration, the filtrate is evaporated and the solid residue used as it is in the following stage.

(d)

1-(3-Aminophenyl)-2-[4-(4-fluorobenzoyl)-1-piperidyl]ethanol.

6.3 g (0.0163 mole) of the above product are introduced into 150 ml of 3 N hydrochloric acid, and the mixture is heated to 100° C. for 2 h on an oil bath. A clear solution is formed, and this is cast into 200 g of ice, ammonia solution is added until the pH is above 8 and the organic base is extracted with ethyl acetate.

The organic phase is washed with water, dried and evaporated, and the reside is purified by chromatography, eluting with a 98:2 chloroform/methanol mixture.

1.35 g of the purified base is dissolved in 25 ml of ethanol and 0.48 g of benzoic acid is added. The benzoate precipitates immediately; it is filtered off and recrystallized in isopropyl alochol.

Melting point of the benzoate: 150° C.

EXAMPLE 12

2-[4-(4-Chlorobenzoyl)-1-piperidyl]-1-(4-ethylphenyl)ethanol (a)

2-Bromo-1-(4-ethylphenyl)ethanone

Bromination of 1-(4-ethylphenyl)ethanone is performed under conditions similar to those described in Example 10b.

(b)

2-{4-[2-(4-Chlorophenyl)-1,3-dioxolan-2-yl]-1-piperidyl}-1-(4-ethylphenyl)ethanol.

5.34 g (0.02 mole) of 4-[2-(4-chlorophenyl)-1,3-dioxolan-2-yl]piperidine, 5.52 g (0.04 mole) of potassium carbonate and 4.35 g (0.02 mole) of the above brominated ketone are introduced into 150 ml of ethanol, and the mixture is heated under reflux for 1 h. The reaction medium is cooled in an ice bath, 10 ml of acetic acid are added and, in small portions, 15 g of potassium borohydride. After the mixture has returned to room temperature, it is left to stand overnight.

The mixture is evaporated, and the residue taken up with water and ammonia solution and extracted with dichloromethane. The organic phase is washed with water, dried and evaporated. The residual oil is purified by chromatography, eluting with a 99:1 dichloromethane/methanol mixture.

(c)

2-[4-(4-Chlorobenzoyl)-1-piperidyl]-1-(4-ethylphenyl)ethanol 5.8 g (0.014 mole) of the above compound are treated at 100° C. with 200 ml of 3 N hydrochloric acid for 3 h, under conditions similar to those of Example 11d. The solution obtained is evaporated and the hydrochloride recrystallized in 75 ml of isopropyl alcohol.

Melting point of the hydrochloride: 252°–254° C.

EXAMPLE 13

2-[4-(4-Chlorobenzoyl)-1-piperidyl]-1-(4-fluorophenyl)propanol, threo form.

(a)

2-{4-[2-(4-Chlorophenyl)-1,3-dioxolan-2-yl]-1-piperidyl}-1-(4-fluorophenyl)propanone.

11.5 g (0.05 mole) of 2-bromo-1-(4-fluorophenyl)propanone are reacted with 13.38 g (0.05 mole) if 4-[2-(4-chlorophenyl)-1,3-dioxolan-2-yl]piperidine in 280 ml of acetonitrile in the presence of 13.9 g (0.1 mole) of potassium carbonate, under conditions similar to those described in Examples 4a, 5a and 10c.

After purification by chromatography, an oil is obtained.

(b)

2-{4-[2-(4-Chlorophenyl)-1,3-dioxolan-2-yl]-1-piperidyl}-1-(4-fluorophenyl)propanol, threo form 8 g (0.019 mole) of the above oil are dissolved in 300 ml of methanol, 16 g of potassium borohydride are added in small portions, and the mixture is stirred for 2 h and left to stand overnight.

The methanol is driven off, and the residue is taken up with water and extracted with ethyl acetate. After the organic phase has been washed with water, dried and evaporated, the residue is purified by chromatography, eluting with a 99:1 dichloromethane/methanol mixture.

A crystallized solid is obtained.

(c)

2-[4-(4-Chlorobenzoyl)-1-piperidyl]-1-(4-fluorophenyl)phenyl)propanol, thereo form.

The above compound is treated with 3 N hydrochloric acid under conditions similar to those described in Example 11d.

The solution obtained is evaporated and the hydrochloride recrystallized in isopropyl alcohol.

Melting point of the hydrochloride: 243°–245° C.

EXAMPLE 14

2-[4-(4-Chlorobenzoyl)-1-piperidyl]-1-(4-fluorophenyl)propanol, erythro form.

2-{4-[2-(4-Chlorophenyl)-1,3-dioxolan-2-yl]-1-piperidyl}-1-(4-fluorophenyl)propanol, erythro form.

6 g of the oil prepared according to Example 13a are dissolved in a mixture of 300 ml of methanol and 150 ml of acetic acid, and 12 g of potassium borohydride are added in small portions. The mixture is stirred for a further 2 h and left to stand. The solvents are evaporated off, water is added and ammonia until the pH is basic, and the mixture is extracted with ethyl acetate. The organic phase is washed, dried and evaporated, and the residue purified by chromatography, eluting with a 99:1 dichloromethane/methanol mixture. A crystallized solid is obtained.

(b)

2-[4-(4-Chlorobenzoyl)-1-piperidyl]-1-(4-fluorophenyl)-propanol, erythro form

The above compound is treated with 3 N hydrochloric acid under conditions similar to those described in Example 11d.

The solution obtained is evaporated and the hydrochloride recrystallized in isopropyl alcohol.

Melting point of the hydrochloride: 242° C.

EXAMPLE 15

Other compounds of the invention produced in similar manner are disclosed in the Table which collates their structures and physical properties with compounds according to Examples 1 to 14.

TABLE

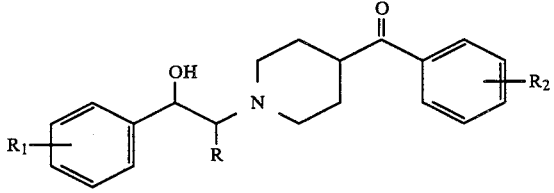

(I)

| Compound | P | $R_1$ | $R_2$ | Isomer | Salt[1] | M.p. (°C.) |
|---|---|---|---|---|---|---|
| 1 (Ex. 1) | H | H | 4-F | (±) | 10 | 218 |
| 2 (Ex. 9) | H | H | 4-F | (+) | 10 | 196–198 |
| 3 (Ex. 8) | H | H | 4-F | (−) | 10 | 205 |
| 4 | H | 4-Cl | H | (±) | 10 | 211–213 |
| 5 (Ex. 2) | H | 4-Cl | 4-F | (±) | 10 | 221–223 |
| 6 | H | 4-Cl | 4-OCH$_3$ | (±) | 10 | 210–212 |
| 7 | H | 4-Cl | 2,4,6-(OCH$_3$)$_3$ | (±) | 10 | 201–202 |
| 8 | H | 3-Cl | 4-F | (±) | 10 | 179–181 |
| 9 | H | 2-Cl | 4-F | (±) | 10 | 212–214 |
| 10 | H | 4-F | H | (±) | 10 | 188 |
| 11 | H | 4-F | 4-F | (±) | 10 | 197–198 |
| 12 | H | 4-F | 3-F | (±) | 10 | 170–172 |
| 13 | H | 3-F | 4-F | (±) | 10 | 178–180 |
| 14 | H | 4-F | 4-Cl | (±) | 10 | 218–220 |
| 15 | H | 4-CF$_3$ | 4-F | (±) | 10 | 226–228 |
| 16 | H | 3-CF$_3$ | 4-F | (±) | 10 | 206–208 |
| 17 | H | 2-CH$_3$ | 4-F | (±) | 10 | 206 |
| 18 (Ex. 3) | H | 3-CH$_3$ | 4-F | (±) | 10 | 226 |
| 19 | H | 4-CH$_3$ | 4-F | (±) | 10 | 240–242 |
| 20 | H | 4-CH$_3$ | 3-F | (±) | 10 | 212 |
| 21 | H | 4-CH$_3$ | H | (±) | 10 | 225–226 |
| 22 | H | 4-CH$_3$ | 4-CH$_3$ | (±) | 10 | 259–260 |
| 23 | H | 4-CH$_3$ | 4-OCH$_3$ | (±) | 10 | 228–229 |
| 24 | H | 3-C$_2$H$_5$ | 4-F | (±) | 10 | 195 |
| 25 | H | 4-C$_2$H$_5$ | 4-F | (±) | 10 | 242–244 |
| 26 (Ex. 12) | H | 4-C$_2$H$_5$ | 4-Cl | (±) | 10 | 252–254 |
| 27 | H | 3-C$_2$H$_5$ | 3-F | (±) | 10 | 179 |
| 28 | H | 4-nC$_4$H$_9$ | 4-F | (±) | 10 | 252–254 |
| 29 (Ex. 4) | H | 4-OCH$_3$ | 4-F | (±) | 10 | 218 |
| 30 | H | 3-OCH$_3$ | 4-F | (±) | 10 | 204 |
| 31 | H | 4-OH | 4-F | (±) | 10 | 185 |
| 32 | H | 4-OnC$_4$H$_9$ | 4-F | (±) | 10 | 243–245 |
| 33 | H | 4-SCH$_3$ | 4-F | (±) | 10 | 221–222 |
| 34 | H | 4-SO$_2$CH$_3$ | 4-F | (±) | 00 | 186–187 |
| 35 | H | 4-NO$_2$ | 4-F | (±) | 10 | 224–226 |
| 36 | H | 3-NO$_2$ | 4-F | (±) | 10 | 214–215 |
| 37 | H | 4-NHCOCH$_3$ | 4-F | (±) | 10 | 210 |
| 38 (Ex. 10) | H | 3-NHCOCH$_3$ | 4-F | (±) | 00 | 158 |
| 39 (Ex. 11) | H | 3-NH$_2$ | 4-F | (±) | 03 | 150 |
| 40 | H | 3-SO$_2$NH$_2$ | 4-F | (±) | 10 | 238 |
| 41 | H | 4-CN | 4-F | (±) | 10 | 235–237 |
| 42 | CH$_3$ | H | 4-F | (±)erythro | 10 | 256–258 |
| 43 | CH$_3$ | H | 4-F | (±)threo | 10 | 216–218 |
| 44 | CH$_3$ | 4-Cl | 4-F | (±)erythro | 10 | 235–236 |
| 45 | CH$_3$ | 4-Cl | 4-F | (±)threo | 10 | 236–237 |
| 46 | CH$_3$ | 3-Cl | 4-F | (±)erythro | 10 | 228–229 |
| 47 | CH$_3$ | 3-Cl | 4-F | (±)threo | 10 | 248–249 |
| 48 | CH$_3$ | 2-Cl | H | (±)erythro | 14 | 192 |
| 49 | CH$_3$ | 2-Cl | 4-F | (±)erythro | 14 | 198 |
| 50 (Ex. 5) | CH$_3$ | 4-F | 4-F | (±)erythro | 10 | 250–252 |

TABLE-continued

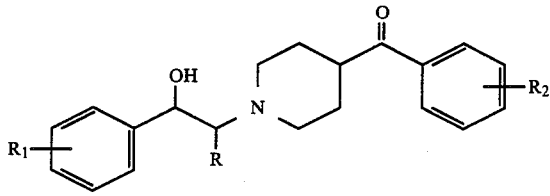

(I)

| Compound | P | $R_1$ | $R_2$ | Isomer | Salt[1] | M.p. (°C.) |
|---|---|---|---|---|---|---|
| 51 (Ex. 6) | $CH_3$ | 4-F | 4-F | (±)threo | 10 | 245–247 |
| 52 (Ex. 14) | $CH_3$ | 4-F | 4-Cl | (±)erythro | 10 | 242 |
| 53 (Ex. 13) | $CH_3$ | 4-F | 4-Cl | (±)threo | 10 | 243–245 |
| 54 | $CH_3$ | 4-F | 4-$CH_3$ | (±)erythro | 10 | 256–257 |
| 55 | $CH_3$ | 4-$CF_3$ | 4-F | (±)erythro | 10 | 264–265 |
| 56 | $CH_3$ | 4-$CF_3$ | 4-F | (±)threo | 10 | 232–234 |
| 57 | $CH_3$ | 4-$CH_3$ | 4-F | (±)erythro | 10 | 265 |
| 58 | $CH_3$ | 4-$CH_3$ | 4-F | (±)threo | 10 | 245 |
| 59 | $CH_3$ | 3-$CH_3$ | 4-F | (±)erythro | 10 | 242–244 |
| 60 | $CH_3$ | 3-$CH_3$ | 4-F | (±)threo | 10 | 232–234 |
| 61 | $CH_3$ | 4-$C_2H_5$ | 4-F | (±)erythro | 10 | 266–268 |
| 62 | $CH_3$ | 4-$C_2H_5$ | 4-F | (±)threo | 10 | 238–240 |
| 63 (Ex. 7d) | $CH_3$ | 4-OH | 4-F | (±)erythro | 10 | 212–214 |
| 64 (Ex. 7c) | $CH_3$ | 4-$OCH_2C_6H_5$ | 4-F | (±)erythro | 10 | 242–244 |
| 65 | $CH_3$ | 4-$NHCOCH_3$ | 4-F | (±)threo | 10 | 223–225 |
| 66 | $CH_3$ | 4-CN | 4-F | (±)erythro | 10 | 256–258 |
| 67 | $CH_3$ | 4-CN | 4-F | (±)threo | 10 | 246–247 |
| 68 | $CH_3$ | 4-$OCH_3$ 3,5-$(CH_3)_2$ | 4-F | (±)erythro | 10 | 262–263 |
| 69 | $CH_3$ | 4-$OCH_3$ 3,5-$(CH_3)_2$ | 4-$CH_3$ | (±)erythro | 10 | 261–262 |

[1] 00: free base
03: benzoate
10: hydrochloride
14: maleate

The compounds of the invention were subjected to pharmacological trials.

Their toxicity was determined in CD1 strain mice by a graphic method. The 50% lethal doses ($LD_{50}$) are, for the most part, greater than 100 mg/kg intraperitoneally.

The compounds of the invention were subjected to the total cerebral ischaemia test. The ischaemia is due to cardiac arrest induced by a rapid intravenous injection of magnesium chloride.

In this test, the "survival time", that is to say the interval between the time of injection of magnesium chloride and the last observable respiratory movement of each mouse, is measured. This last movement is considered to be the final index of functioning of the central nervous system. The respiratory arrest appears approximately 19 seconds after the injection of magnesium chloride.

Male mice (Charles River CD1) are studied in groups of 10. The mice are supplied with food and water ad libitum before the trials. The survival time is measured 10 minutes after the intraperitoneal administration of the compounds of the invention.

The results are given in the form of the difference between the survival time measured in a group of 10 mice which received the compound, and the survival time measured in a group of 10 mice which received the vehicle liquid. The ratios between the modifications in the survival period and the dose of the compound are recorded graphically on a semi-logarithmic curve.

By means of this curve, it is possible to calculate the 3 seconds' effective dose ($ED_3''$), that is to say the dose (in mg/kg) which produces an increase of 3 seconds in the survival time relative to the control group of 10 untreated mice.

An increase of 3 seconds in the survival time is both statistically significant and reproducible.

The $ED_3''$ values of the compounds of the invention range from 0.5 to 10 mg/kg i.p.

The compounds of the invention were also subjected to a test of displacement of the binding of spiroperidol to the serotoninergic (5-$HT_2$) receptors of the rat cerebral cortex.

For this test, the brains were removed from rats, and the cortex was dissected out and homogenized at 0° C. in 50 volumes of a mixture containing, per liter, 50 millimoles of Tris.HCL buffer, pH 7.4, 120 millimoles of sodium chloride and 5 millimoles of potassium chloride. The homogeneous mixture is centrifuged at 40,000xg for 10 minutes, and the pellet is then recovered, washed by being suspended in the same buffer mixture, homogenized again and centrifuged, this procedure being repeated a second time. The procedure is completed by diluting the final pellet in the same buffer mixture, in the proportion of 10 mg of wet tissue for 1 ml of buffer.

The tissue is then subjected to a prior incubation for 5 minutes at 37° C. in the presence of 0.1% of ascorbic acid and 10 micromoles/l of pargyline, followed by an incubation for 20 minutes at 37° C. in the presence of [$^3$H]spiroperidol (specific activity: 25.6 Ci/millimole) at a concentration of 0.3 nanomole/l and test compound at concentrations ranging from 0.0001 to 100 micromoles/l.

1 ml aliquots are withdrawn and filtered under vacuum, and the filters are washed twice with 5 ml of cold buffer and dried. The radioactivity is measured in toluene in the presence of 5 g/l of 2,5-diphenyloxazole (PPO) and 0.1 g/l of 1,4-bis(5-phenyl-2-oxazolyl) benzene (POPOP).

To assess the activity of the compounds, a curve is established for the percentage inhibition of the specific binding of [³H]spiroperidol in terms of the concentration of the displacing drug. The IC$_{50}$ concentration, the concentration which 50% inhibits the specific binding, is determined graphically. The specific binding is defined as the binding displaced by 100 micromoles/l of 5-HT.

The IC$_{50}$ concentrations of the compounds of the invention lie between 0.01 and 3.6 micro-mole/l.

Finally, the compounds of the invention were subjected to a test of displacement of the binding of prazosin (an antihypertensive agent) to the alpha$_1$ receptors of the rat cerebral cortex.

Rat cortex is homogenized in 30 volumes of Tris.HCl buffer (50 millimoles/l, pH 7.5) for 30 seconds, and centrifugation is performed at 45,000xg for 10 minutes. The pellet is resuspended in the buffer, homogenized and centrifuged a further time under the same conditions.

Finally, the membranes are suspended in 100 volumes of the same buffer to obtain a final concentration of 10 mg of wet tissue per ml (equivalent to 0.55 mg of protein per ml).

1 ml portions of the suspension are then incubated for 30 minutes at 25° C. in the presence of 0.5 nanomole/l of [³H]prazosin (specific activity: 25.4 Ci/millimole) and test compounds at concentrations ranging from 0.0001 to 100 micromoles/l.

After incubation, 0.45 ml of each mixture is diluted in 3 ml of buffer, the suspension is rapidly filtered and the residue is washed twice with 5 ml of cold buffer. The filters are dried and the radioactivity is measured by scintillation spectrometry. For each compound, a curve is established for the percentage inhibition of the binding of [³H]prazosin in terms of the concentration of the displacing drug, and the IC$_{50}$ concentration, the concentration which 50% inhibits the specific binding, is determined graphically.

The specific binding is defined as the binding displaced in the presence of 10 micromoles/l of phentolamine.

The IC$_{50}$ concentrations of the compounds of the invention lie between 0.01 and 10 micromoles/l.

We claim:

1. A compound of formula (I)

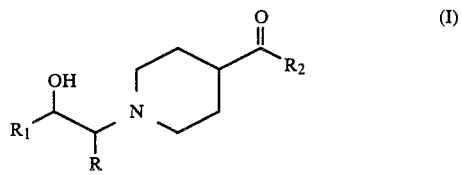

in which R is hydrogen or methyl, R$_1$ is unsubstituted phenyl, 4-methoxy-3,5-dimethyl phenyl or phenyl substituted at one of the 2-, 3- or 4-positions by halogen, C$_{1-4}$ alkyl, C$_{1-4}$ alkoxy, hydroxy, benzyloxy, trifluoromethyl, cyano, nitro, amino, acetylamino, methylthio, methylsulphonyl or aminosulphonyl and R$_2$ is unsubstituted phenyl, 2,4,6-trimethoxyphenyl or phenyl substituted at either the 3- or the 4-position by fluorine, chlorine, methyl or methoxy, or a pharmaceutically acceptable, acid addition salt thereof.

2. A compound according to claim 1 wherein R$_1$ is halogenophenyl or alkyl phenyl and R$_2$ is fluorophenyl.

3. A compound according to claim 1 in the form of a pure optical isomer.

4. A pharmaceutical formulation comprising a compound according to claim 1 and a pharmaceutically acceptable excipient.

5. A pharmaceutical composition according to claim 4 presented in unit dosage form for oral administration or as a solution for parental administration.

6. A method for treating humans or non-human animals suffering from anoxia comprising adminstering an amount of a compound of formula (I) as defined in claim 1 to a human or animal need thereof effective for the treatment of anoxia.

7. A method according to claims 6 for treating anoxic disorders.

8. A method according to claim 6 for treating humans comprising parentally administering from 1 to 100 mg of a compound of formula (I) per day.

9. A method according to claim 6 for treating humans comprising orally administering from 5 to 500 mg of a compound of formula (I) per day.

* * * * *